US010450850B2

United States Patent
Roberson et al.

(10) Patent No.: US 10,450,850 B2
(45) Date of Patent: Oct. 22, 2019

(54) DUAL-FREQUENCY TAGS TO DETECT CEMENT CURING IN WELLBORE APPLICATIONS

(71) Applicant: Halliburton Energy Services, Inc., Houston, TX (US)

(72) Inventors: Mark W. Roberson, Houston, TX (US); Scott Goodwin, Chapel Hill, NC (US); Krishna M. Ravi, Houston, TX (US)

(73) Assignee: Halliburton Energy Sevices, Inc., Houston, TX (US)

( * ) Notice: Subject to any disclaimer, the term of this patent is extended or adjusted under 35 U.S.C. 154(b) by 131 days.

(21) Appl. No.: 15/532,003

(22) PCT Filed: Feb. 20, 2015

(86) PCT No.: PCT/US2015/016825
§ 371 (c)(1),
(2) Date: May 31, 2017

(87) PCT Pub. No.: WO2016/133537
PCT Pub. Date: Aug. 25, 2016

(65) Prior Publication Data
US 2018/0283164 A1 Oct. 4, 2018

(51) Int. Cl.
*E21B 47/00* (2012.01)
*G01V 1/44* (2006.01)
(Continued)

(52) U.S. Cl.
CPC .......... *E21B 47/0005* (2013.01); *E21B 33/14* (2013.01); *G01N 29/12* (2013.01);
(Continued)

(58) Field of Classification Search
CPC ....... E21B 47/0005; E21B 33/14; G01V 1/44; G01N 29/12; G01N 2291/0251; G01N 2291/014; G06K 19/0672
See application file for complete search history.

(56) References Cited

U.S. PATENT DOCUMENTS 7,038,470 B1   5/2006   Johnson
8,368,514 B2   2/2013   Wiberg et al.
(Continued)

FOREIGN PATENT DOCUMENTS

CA   2827763 A1   8/2012

OTHER PUBLICATIONS

International Search Report and the Written Opinion of the International Search Authority, or the Declaration, dated Oct. 29, 2015, PCT/US2015/016825, 15 pages, ISA/KR.
(Continued)

*Primary Examiner* — Wei Wang
(74) *Attorney, Agent, or Firm* — Haynes and Boone, LLP (57) ABSTRACT

Micro-Electro-Mechanical System ("MEMS") tags having high and low resonant frequencies are used to detect the cured or uncured state of wellbore cement. The MEMS tags may be added to wellbore cement, and pumped downhole. An interrogation tool emits a signal at one or both of the resonant frequencies which, in turn, interacts with the MEMS tags to produce a response signal. Since uncured cement has a high attenuation, only the lower resonant frequency response signal is sensed by an interrogation device, thus indicating the cement remains uncured. When the cement cures, its conductivity drops and the attenuation of the higher resonant frequency response signal drops also, thus allowing that signal to be detected by the interrogation device and indicating the cement has cured.

6 Claims, 4 Drawing Sheets (51) Int. Cl.
  *E21B 33/14*    (2006.01)
  *G01N 29/12*    (2006.01)
  *G06K 19/067*   (2006.01)

(52) U.S. Cl.
  CPC ........... *G01V 1/44* (2013.01); *G06K 19/0672* (2013.01); *G01N 2291/014* (2013.01); *G01N 2291/0251* (2013.01)

(56) References Cited

U.S. PATENT DOCUMENTS

| | | | |
|---|---|---|---|
| 9,732,584 B2 * | 8/2017 | Roddy | .................... E21B 33/13 |
| 2004/0167248 A1 | 8/2004 | Brothers et al. | |
| 2005/0241855 A1 | 11/2005 | Wylie et al. | |
| 2011/0285511 A1 | 11/2011 | Maguire et al. | |
| 2014/0354443 A1 | 12/2014 | Roberson et al. | |

OTHER PUBLICATIONS

Office Action issued for Canadian Patent Application No. 2,974,251, dated Jun. 26, 2018, 6 pages.

* cited by examiner

DUAL-FREQUENCY TAGS TO DETECT CEMENT CURING IN WELLBORE APPLICATIONS

PRIORITY

The present application is a U.S. National Stage patent application of International Patent Application No. PCT/US2015/016825, filed on Feb. 20, 2015, the benefit of which is claimed and the disclosure of which is incorporated herein by reference in its entirety.

FIELD OF THE DISCLOSURE

The present disclosure generally relates to downhole completions and, more particularly, to dual-frequency Micro-Electro-Mechanical System ("MEMS") tags used to detect cement curing.

BACKGROUND

Natural resources such as gas, oil, and water residing in a subterranean formation or zone are usually recovered by drilling a wellbore into the subterranean formation while circulating a drilling fluid in the wellbore. After terminating the circulation of the drilling fluid, a string of pipe (e.g., casing) is run in the wellbore. The drilling fluid is then usually circulated downward through the interior of the pipe and upward through the annulus, which is located between the exterior of the pipe and the walls of the wellbore. Next, primary cementing is typically performed whereby a cement slurry is placed in the annulus and permitted to set into a hard mass (i.e., sheath) to thereby attach the string of pipe to the walls of the wellbore and seal the annulus.

Subsequent secondary cementing operations may also be performed. One example of a secondary cementing operation is squeeze cementing, whereby a cement slurry is employed to plug and seal off undesirable flow passages in the cement sheath and/or the casing. Non-cementous sealants are also utilized in preparing a wellbore. For example, polymer, resin, or latex-based sealants may be desirable for placement behind casing.

To enhance the life of the well and minimize costs, sealant slurries are chosen based on calculated stresses and characteristics of the formation to be serviced. Suitable sealants are selected based on the conditions that are expected to be encountered during the sealant service life. Once a sealant is chosen, it is desirable to monitor and/or evaluate the health of the sealant so that timely maintenance can be performed and the service life maximized. The integrity of sealant can be adversely affected by conditions in the well. For example, cracks in cement may allow water influx while acid conditions may degrade cement. The initial strength and the service life of cement can be significantly affected by its moisture content from the time that it is placed. Moisture and temperature are the primary drivers for the hydration of many cements and are critical factors in the most prevalent deteriorative processes, including damage due to freezing and thawing, alkali-aggregate reaction, etc.

Accordingly, an ongoing need exists for methods of monitoring wellbore sealant conditions from placement through the service lifetime of the sealant.

DESCRIPTION OF ILLUSTRATIVE EMBODIMENTS

Illustrative embodiments and related methods of the present disclosure are described below as they might be employed in a dual frequency MEMS tag utilized to detect cured cement. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the disclosure will become apparent from consideration of the following description and drawings.

As described herein, illustrative embodiments of the present disclosure are directed to MEMS tags and related methods to detect the cured or uncured state of wellbore cement. In a first generalized embodiment, a MEMS tag with two different resonant frequencies is provided. One of the resonant frequencies may be lower than 800 MHz, while the second resonant frequency may be higher than 800 MHz. The MEMS tag comprises a planar structure having one or more circuits suitable to generate the two resonant frequencies.

In a generalized method, one or more MEMS tags are mixed into a wellbore cement mixture, and the mixture is pumped downhole into the wellbore annulus. The MEMS tags include circuitry that resonates at a high and low resonant frequency. When pumping is complete (or during pumping), an interrogation tool, which may be deployed downhole or form part of the downhole completion system (e.g., positioned on the casing), interrogates the MEMS tags in the annulus using radio frequency ("RF") signals emitted at the two resonant frequencies. In turn, the MEMS tags are activated, whereby they interact with the two high resonant frequency RF signals, thereby resulting in a response signal. If the RF signal emitted from the interrogation tool is the same frequency as one of the two resonant tag frequencies, the circuit will begin to resonant which will absorb power from the emitted signal, thus resulting in a response signal having less power than the emitted signal. The interrogation tool can then detect this response signal, which also indicates the presence of the MEMS tag.

Since uncured cement has a high attenuation, only the lower resonant frequency response signal is sensed by the interrogation device, thus indicating the cement remains uncured. When the cement cures, however, its conductivity drops and the attenuation of the higher resonant frequency response signal drops also, thus allowing that signal to be detected by the interrogation device—thus indicating the cement has cured. Accordingly, the two response signals are used to detect the cured or uncured state of the cement. Such information is useful in, among others, determining the integrity of the cured cement. In yet other methods, the location of the MEMS tags along the annulus may also be determined using the high frequency response signals.

Figure 1A:
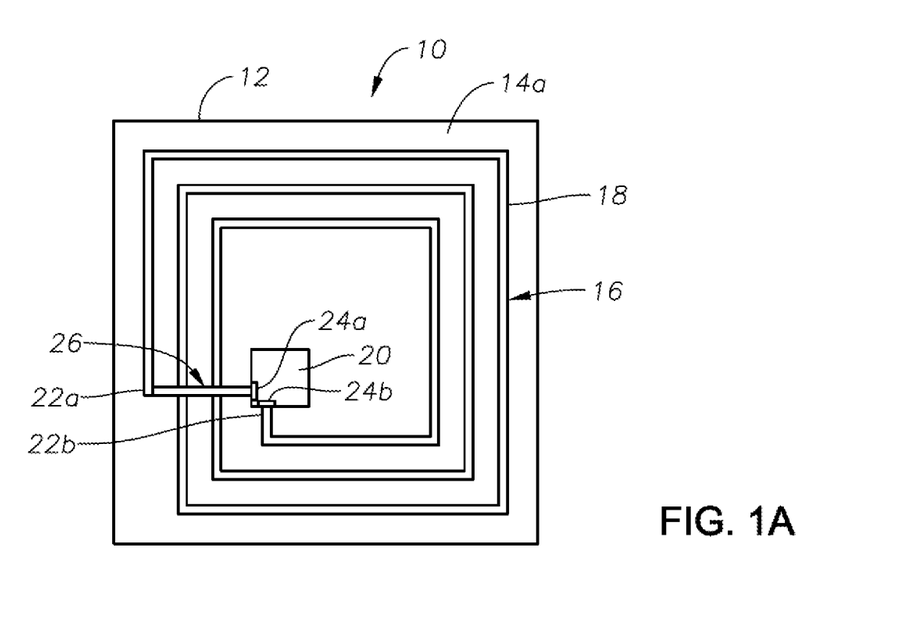
FIGS. 1A and 1B show a first and second side, respectively, of a single MEMS tag, according to certain illustrative embodiments of the present disclosure.
Figure 1B:
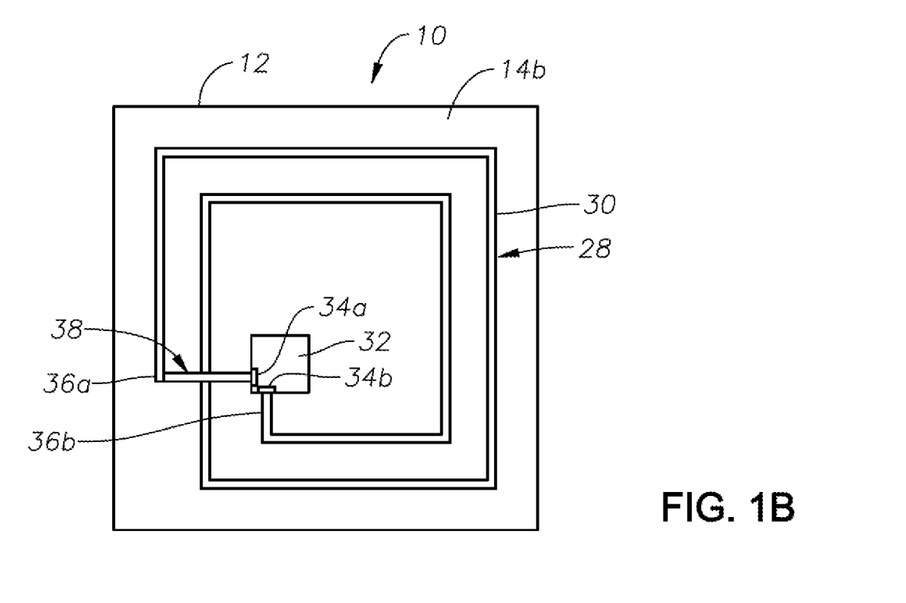

FIGS. 1A and 1B show a first and second side, respectively, of a single MEMS tag, according to certain illustrative embodiments of the present disclosure. MEMS tag 10 is comprised of a planar structure 12 having a first side 14a and a second side 14b. Planar structure 12 is a low loss tangent structure, such as, for example, quartz, sapphire, polyethylene, polystyrene or Teflon.

MEMS tag 10 includes circuitry that resonates at two different resonant frequencies, and may also be referred to as a "dual transponder". In certain illustrative embodiments, the first resonant frequency may be lower than 800 MHz, while the second resonant frequency may be greater than 800 MHz. In general, however, one of the resonant frequencies is below a frequency in which the signal efficiently propagates, while the other resonant frequency is above the frequency in which the RF signals are attenuated. First side 14a of planar structure 12 includes an inductor-capacitor circuit ("LC circuit") 16 which includes an inductor 18 connected to a capacitor 20. Inductor 18 may be comprised of a variety of low resistivity materials, such as, for example, copper. Inductor 18 includes a first end 22a and a second end 22b. Capacitor 20 includes a first conductive plate 24a and a second conductive plate 24b. Second conductive plate 24 is connected to second end 22b of inductor 18, while first conductive plate 24a is connected to a return trace 26, which provides a connection to first end 22a of inductor 18. Return trace 26 is electrically insulated from inductor 18 (except for first end 22a).

Referring to FIG. 1B, MEMS tag 18 also includes a second LC circuit 28 on second side 14b. Second LC circuit 28 is constructed similarly to first LC circuit 16, however inductor 30 has less turns than inductor 18. Capacitor 32 also includes first and second conductive plates 34a,b, which are connected to second end 36b of inductor 30 and return trace 38 (which connects first end 36a of inductor 30 to first conductive plate 34a.

Referring to FIGS. 1A and 1B, first and second LC circuits 16,28 have a different number of inductor turns. First LC circuit 16 has three turns, while second LC circuit 28 has two turns. The inductance is a strong function of the number of turns in the inductor, thus the inductor 18 has more inductance than the inductor 30. The capacitance of the capacitors is strongly dependent on the area of the capacitor, thus the capacitor 20 has more capacitance than capacitor 32. The resonant frequency of the LC circuit is to first order equal to $1/(2\pi sqrt(LC))$, so larger values of the LC product result in lower resonant frequencies and the LC circuit 16 will resonate at a lower frequency than LC circuit 28. As a result, first and second LC circuits 16,28 are tuned to different resonant frequencies. In certain illustrative embodiments, the resonant frequencies are greater than 800 MHz, while the other is less than 800 MHz. Moreover, the size of MEMS tag 10 is within the range of 1 mm-10 mm square, in certain embodiments. Although described as planar, MEMS tag 10 may take different shapes and/or sizes, as will be understood by those ordinarily skilled in the art having the benefit of this disclosure. Additionally, although described as LC circuits, the circuits described herein may include other designs sufficient to generate the resonant frequencies.

Figure 2A:
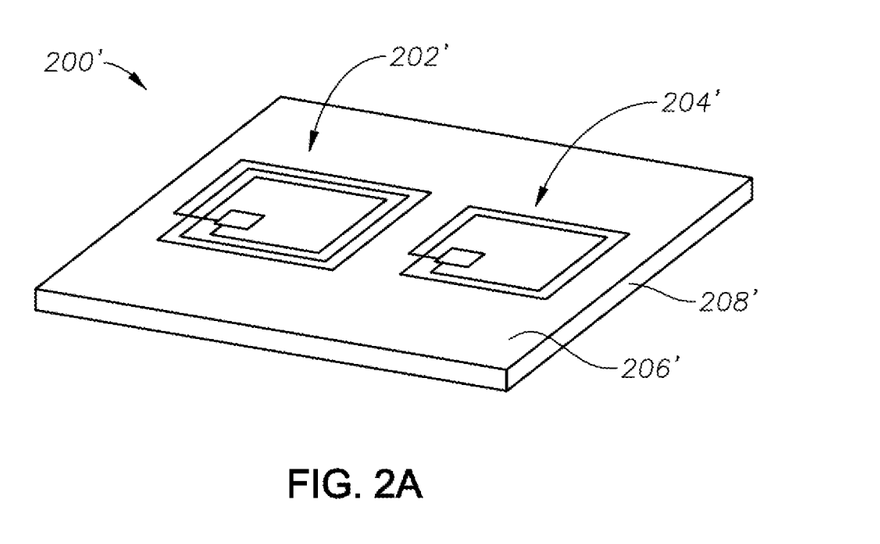
FIGS. 2A and 2B illustrate alternative MEMS tag designs, according to certain illustrative embodiments of the present disclosure.

FIGS. 2A and 2B illustrate alternative MEMS tag designs, according to certain illustrative embodiments of the present disclosure. In FIG. 2A, MEMS tag 200' includes a first circuit 202' and second circuit 204' on a first side 206' of planar structure 208', arranged in a side-by-side fashion. First and second circuits 202',204' may be designed similarly to earlier described circuits. In this example, first circuit 202' resonates at the first resonant frequency, while second circuit 204' resonates at the second resonant frequency. In an alternate embodiment, MEMS tag 200' may comprise a third and fourth circuit (not shown) on its second side. The third and fourth circuits may be identical to first and second circuits 202',204', thus allowing MEMS tag 200' to be more easily detected through a stronger interaction with the interrogation tool.

Figure 2B:
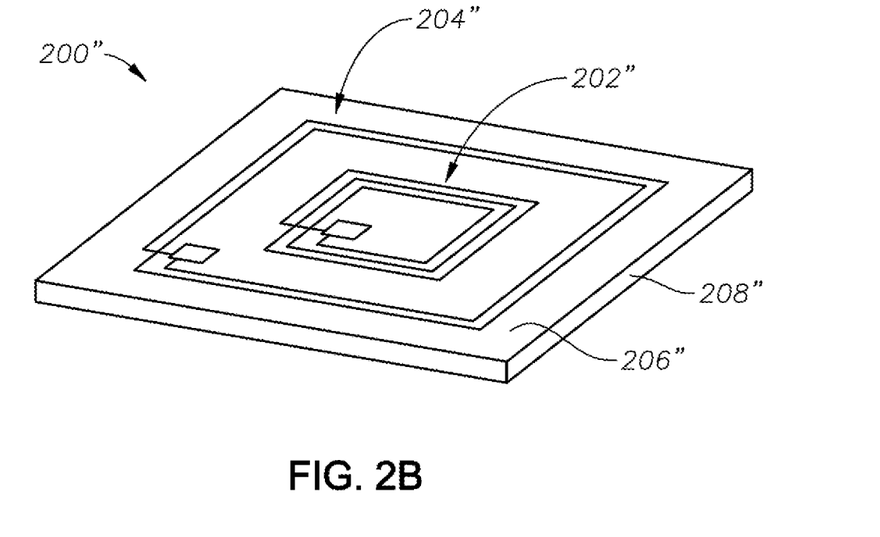

In FIG. 2B, MEMS tag 200" also includes a first circuit 202" and second circuit 204" positioned on first side 206" of planar structure 208". First and second circuits 202",204" resonate at a first and second resonant frequency, as previously described. In this example, however, second circuit 202" is positioned inside first circuit 204" (i.e., circuit 202" resides inside the innermost turn of the inductor of circuit 204"). In an alternate embodiment, MEMS tag 200" may comprise a third and fourth circuit (not shown) on its second side. The third and fourth circuits may be identical to first and second circuits 202",204", thus allowing MEMS tag 200" to be more easily detected through a stronger interaction with the interrogation tool.

The features of FIGS. 2A and 2B may be combined as desired. For example, in certain embodiments, the first and second circuits may combinatorily resonate at the first resonant frequency, while the third and fourth circuits combinatorily resonate at the second resonant frequency. Alternatively, circuits on opposing sides of the planar structure may resonate at the same frequencies. Those ordinarily skilled in the art having the benefit of this disclosure will realize the features described herein may be combined in a variety of ways.

Now that illustrative embodiments of the MEMS tags have been described, applications in which they can be utilized will be described. Although the dual-frequency MEMS tags can be used in a variety of applications, the following description will focus on wellbore applications. Discussion of an illustrative method of the present disclosure will now be made with reference to FIG. 3, which is a flow chart of a method for placing dual-frequency MEMS tags in a wellbore and gathering data.

Figure 3:
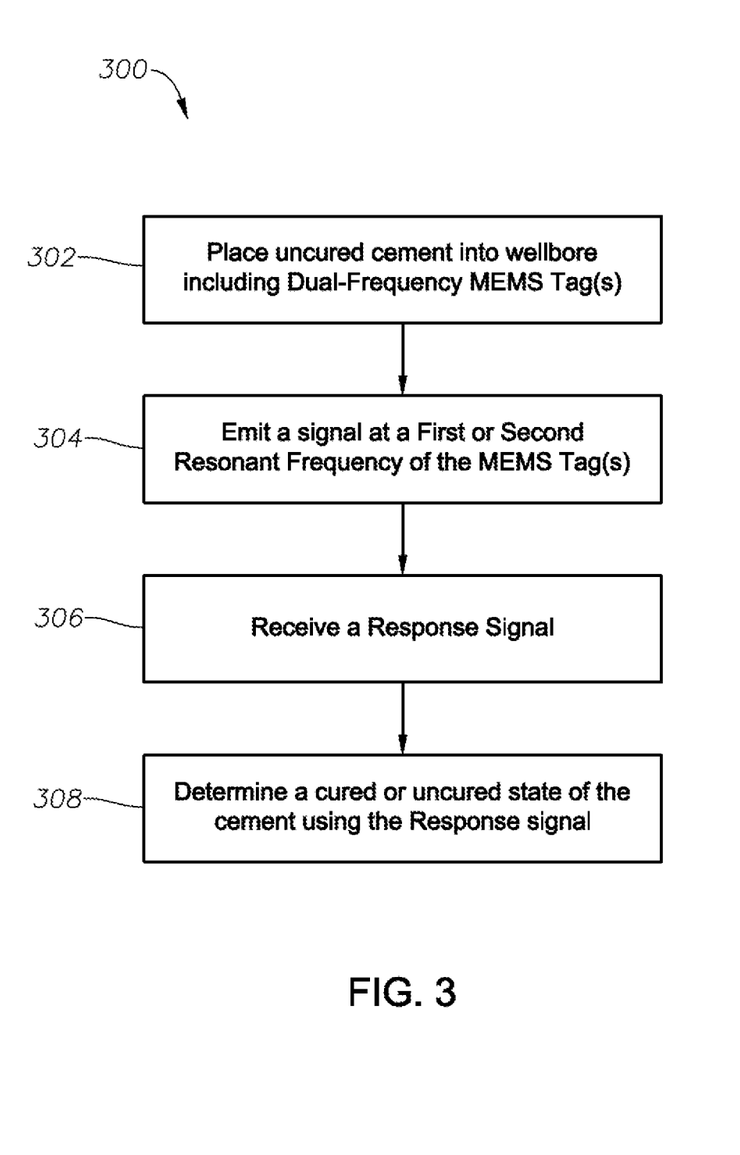
FIG. 3 is a flow chart of a method for placing dual-frequency MEMS tags in a wellbore and gathering data, according to certain illustrative methods of the present disclosure.

To begin the method, one or more dual-frequency MEMS tags are added to a mixture of cement, and the uncured cement is placed into the wellbore at block 302. In certain embodiments, the MEMS tags may be mixed with a dry material, mixed with one more liquid components (e.g., water or a non-aqueous fluid), or combinations thereof. The mixing may occur onsite, for example addition of the MEMS tags into a bulk mixer such as a cement slurry mixer. The MEMS tags may be added directly to the mixer, may be added to one or more component streams and subsequently fed to the mixer, may be added downstream of the mixer, or combinations thereof.

As the cement is pumped downhole at block 302, the MEMS tags are positioned within the wellbore. For example, the MEMS tags may extend along all or a portion of the length of the wellbore adjacent the casing (e.g., casing/wellbore annulus). The cement may be placed downhole as part of a primary cementing, secondary cementing, or other sealant operation. At block 304, a data interrogator tool is positioned in an operable location to gather data from the MEMS tags, for example lowered within the wellbore proximate the MEMS tags or already positioned downhole as part of the completion (e.g., on casing string).

The data interrogator tool interrogates the MEMS tags (e.g., by emitting an RF signal at the first and/or second resonant frequencies of the MEMS tags) at block 304. The MEMS tags are thereby activated to interact with the first and/or second resonant frequencies, as previously described, whereby one or both response signals are received by the interrogation tool at block 306. One of the signals may be transmitted at a frequency of greater than 800 MHz, while the other signal is transmitted at a frequency of lower than 800 MHz, for example. As previously described, since uncured cement has a high attenuation, only the lower resonant frequency response signal is sensed while the cement is uncured. When the cement cures, however, its conductivity drops and the attenuation of the higher resonant frequency response signal drops also, thus allowing that response to be detected by the interrogation device—thus indicating the cement has cured.

Once the response signal(s) has been received, the interrogation tool communicates the resonant frequency response signals to one or more computer components (e.g., memory and/or microprocessor) that may be located within the tool, at the surface, or both. At block 308, the response signals may be used locally or remotely from the tool to determine the cured or uncured state of the cement, as previously described. Moreover, the location of each MEMS tag can be determined and correlated to the data received (the response signals may carry a variety of data) in order to evaluate cement sealant integrity.

In certain illustrative embodiments, the MEMS tags described herein are passive sensors that do not require continuous power from a battery or an external source in order to transmit real-time data over the dual resonant frequencies. The MEMS tags are micro-electromechanical systems comprising one or more (and typically a plurality of) mechanical features on the micrometer scale. In addition to the LC circuits described herein, the MEMS tags may embody the integration of mechanical elements, sensors, actuators, and electronics on a common substrate. In embodiments, the substrate may comprise quartz.

In certain illustrative embodiments, as previously described, the MEMS tags comprise passive (remain unpowered when not being interrogated) sensors energized by energy radiated from a data interrogation tool. The data interrogation tool, which may be a deployed tool or form part of the downhole completion itself, may comprise an energy transceiver sending energy (e.g., RF waves) to the MEMS tags and receiving response signals, as well as a processor for processing the received signals. The data interrogation tool may further comprise a memory component, a communications component, or both. The memory component may store raw and/or processed data received from the MEMS tags, and the communications component may transmit raw data to the processor and/or transmit processed data to another receiver, for example located at the surface.

Figure 4:
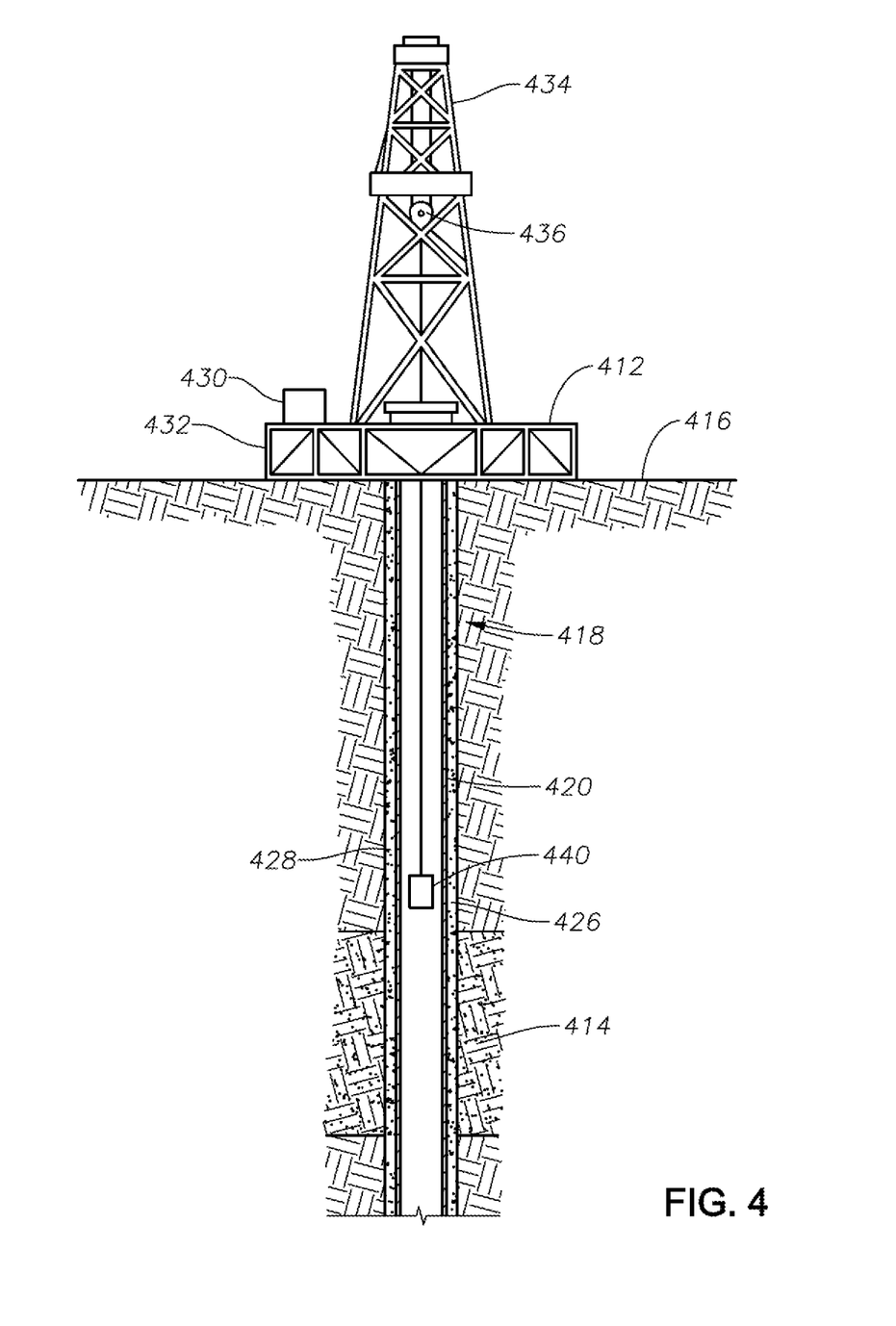
FIG. 4 shows an onshore oil or gas drilling rig and wellbore application in which embodiments of the present disclosure may be used.

FIG. 4, which shows an onshore oil or gas drilling rig and wellbore, will be used to further describe illustrative methods of the present disclosure. Rig 412 is centered over a subterranean oil or gas formation 414 located below the earth's surface 416. Rig 412 includes a work deck 432 that supports derrick 434. Derrick 434 supports a hoisting apparatus 436 for raising and lowering pipe strings such as casing 420. Pump 430 is capable of pumping a variety of wellbore compositions (e.g., drilling fluid or cement) into the well and includes a pressure measurement device that provides a pressure reading at the pump discharge.

Wellbore 418 has been drilled through the various earth strata, including formation 414. Upon completion of wellbore drilling, casing 420 is placed in wellbore 418 to facilitate the production of oil and gas from formation 414. Casing 420 is a string of pipes that extends down wellbore 418, through which oil and gas will eventually be extracted. The region between casing 420 and the wall of wellbore 418 is known as the casing annulus 426. To fill up casing annulus 426 and secure casing 420 in place, casing 420 is usually "cemented" in wellbore 418, which is referred to as "primary cementing." A data interrogation tool 440 is shown in wellbore 418, however in other embodiments interrogation tool 440 may be positioned along casing 420 or otherwise positioned downhole.

In certain illustrative embodiments of the present disclosure, the MEMS tags may be used for monitoring primary cement during and/or subsequent to a conventional primary cementing operation. In this conventional primary cementing embodiment, MEMS tags are mixed into an uncured cement slurry, and the uncured cement slurry is then pumped (by pump 430) down the inside of casing 420. As the slurry reaches the bottom of casing 420, it flows out of casing 420 and into casing annulus 426 between casing 420 and the wall of wellbore 418. As cement slurry 428 flows up annulus 426, it displaces any fluid in the wellbore. To ensure no cement remains inside casing 420, devices called "wipers" may be pumped by a wellbore servicing fluid (e.g., drilling mud) through casing 420 behind cement slurry 428. The wiper contacts the inside surface of casing 420 and pushes any remaining cement out of casing 420. When cement slurry 428 reaches the earth's surface 416, and annulus 426 is filled with slurry, pumping is terminated and the cement is allowed to cure/set.

During cementing, or subsequent to the setting of cement slurry 428, data interrogation tool 440 may be positioned in wellbore 418. For example, the wiper may be equipped with a data interrogation tool and may read the dual-frequency data from the MEMS tags while being pumped downhole and transmit the same to the surface. Alternatively, an interrogation tool may be run into the wellbore following completion of cementing a segment of casing, for example as part of the drill string during resumed drilling operations. Alternatively, the interrogator tool may be run downhole via a wireline or other conveyance (e.g., logging-while-drilling assembly), or may form a permanent part of casing 420.

Nevertheless, data interrogation tool 440 may then be signaled to interrogate the MEMS tags along annulus 426 using the dual high and low-frequency signals. As previously described, the MEMS tags will interact with the emitted signals to generate response signals that indicate the cured or uncured nature of the cement. Data interrogation tool 440 communicates the response signal data to a local or remote processor, whereby the MEMS tag (and likewise cement slurry) position and cement integrity may be determined.

As previously described, the dual-frequency signals may be used to determine if the cement is cured or uncured, and the location of such states along annulus 426. Since uncured cement has a high attenuation, only the lower resonant frequency response signal is sensed by the interrogation device, thus indicating the cement remains uncured. When the cement cures, its conductivity drops and the attenuation of the higher resonant frequency response signal drops also, thus allowing that signal to be detected by the interrogation device—thus indicating the cement has cured.

Also, the response signal data may reveal conditions that may be adverse to cement curing, such as, for example, temperature profiles. Alternatively, such data may indicate a zone of reduced, minimal, or missing MEMS tags, which would indicate a loss of cement corresponding to the area (e.g., a loss/void zone or water influx/washout). Moreover, such methods may be used with various other cement techniques, such as, for example, reverse primary cementing.

Embodiments described herein further relate to any one or more of the following paragraphs:

1. A method to detect curing of cement in a wellbore, the method comprising placing cement into the wellbore, the cement comprising one or more Micro-Electro-Mechanical System ("MEMS") tags which resonate at a first resonant frequency and a second resonant frequency different from the first resonant frequency; emitting a signal into the wellbore at the first or second resonant frequency, wherein the signal interacts with the MEMS tags to produce a response signal; receiving the response signal; and determining whether the cement is uncured or cured based upon the response signal.
2. A method as defined in paragraph 1, wherein the first resonant frequency is a frequency below which the signal efficiently propagates; and the second resonant frequency is a frequency above which the signal is attenuated.
3. A method as defined in paragraphs 1 or 2, wherein emitting the signal comprises emitting the signal at a first resonant frequency lower than 800 MHz.
4. A method as defined in any of paragraphs 1-3, wherein emitting the signal comprises emitting the signal at a second resonant frequency higher than 800 MHz.
5. A method as defined in any of paragraphs 1-4, wherein placing the cement into the wellbore comprises pumping the cement into an annulus of the wellbore; and receiving the response signal comprises utilizing an interrogation tool to receive the response signal.
6. A method as defined in any of paragraphs 1-5, wherein placing the cement into the wellbore is achieved using a pump.
7. A Micro-Electro-Mechanical System ("MEMS") tag, comprising circuitry to resonate at a first resonant frequency; and circuitry to resonate at a second resonant frequency different from the first resonant frequency.
8. A MEMS tag as defined in paragraph 7, wherein the first resonant frequency is a frequency below which the signal efficiently propagates; and the second resonant frequency is a frequency above which the signal is attenuated.
9. A MEMS tag as defined in paragraphs 7 or 8, wherein the first resonant frequency is lower than 800 MHz.
10. A MEMS tag as defined in any of paragraphs 7-9, wherein the second resonant frequency is higher than 800 MHz.
11. A MEMS tag as defined in any of paragraphs 7-10, wherein the circuitry which resonates at the first and second resonant frequencies comprises an LC circuit.
12. A MEMS tag as defined in any of paragraphs 7-11, wherein a size of the MEMs tag is in a range of 1 mm-10 mm.
13. A MEMS tag as defined in any of paragraphs 7-12, wherein the MEMS tag comprises a planar structure having a first and second side; and the circuitry which resonates at the first and second resonant frequencies comprises: a first circuit on the first side; and a second circuit on the second side.
14. A MEMS tag as defined in any of paragraphs 7-13, wherein the MEMS tag comprises a planar structure having a first and second side; and the circuitry which resonates at the first and second resonant frequencies comprises: a first circuit on the first side; and a second circuit on the first side.
15. A MEMS tag as defined in any of paragraphs 7-14, wherein the second circuit is positioned inside the first circuit.
16. A MEMS tag as defined in any of paragraphs 7-15, wherein a third and fourth circuit are positioned on the second side; the third circuit is positioned inside the fourth circuit; the first and second circuits combinatorily resonate at the first resonant frequency; and the third and fourth circuits combinatorily resonate at the second resonant frequency.
17. A MEMS tag as defined in any of paragraphs 7-16, wherein the first and second circuits are positioned side-by-side.
18. A MEMS tag as defined in any of paragraphs 7-17, wherein: the MEMS tag comprises a planar structure having a first and second side; and the circuitry which resonates at the first and second resonant frequencies comprises: a first and second circuit on the first side to combinatorily resonate at the first resonant frequency; and a third and fourth circuit on the second side to combinatorily resonate at the second resonant frequency.
19. A MEMS tag as defined in any of paragraphs 7-18, wherein the MEMS tag comprises part of a wellbore cement mixture.
20. A method to detect curing of cement in a wellbore using one or more Micro-Electro-Mechanical System ("MEMS") tags as defined in any of paragraphs 7-19.

Although various embodiments and methodologies have been shown and described, the disclosure is not limited to such embodiments and methodologies and will be understood to include all modifications and variations as would be apparent to one skilled in the art. For example, in addition to detecting cement curing in downhole applications, the illustrative MEMS tags described herein may also be used to detect other phenomena such as, for example, curing of concrete structures (e.g., office buildings, etc.). Therefore, it should be understood that embodiments of the disclosure are not intended to be limited to the particular forms disclosed. Rather, the intention is to cover all modifications, equivalents and alternatives falling within the spirit and scope of the disclosure as defined by the appended claims.

What is claimed is:

1. A method to detect curing of cement in a wellbore, the method comprising:
    placing cement into the wellbore, the cement comprising one or more Micro-Electro-Mechanical System ("MEMS") tags which resonate at a first resonant frequency and a second resonant frequency different from the first resonant frequency;
    emitting a signal into the wellbore at the first or second resonant frequency, wherein the signal interacts with the MEMS tags to produce a response signal;
    receiving the response signal; and
    determining whether the cement is uncured or cured based upon the response signal.
2. A method as defined in claim 1, wherein:
    the first resonant frequency is a frequency below which the signal efficiently propagates; and
    the second resonant frequency is a frequency above which the signal is attenuated.
3. A method as defined in claim 1, wherein emitting the signal comprises emitting the signal at the first resonant frequency lower than 800 MHz.

4. A method as defined in claim 1, wherein emitting the signal comprises emitting the signal at the second resonant frequency higher than 800 MHz.

5. A method as defined in claim 1, wherein:
placing the cement into the wellbore comprises pumping the cement into an annulus of the wellbore; and
receiving the response signal comprises utilizing an interrogation tool to receive the response signal.

6. A method as defined in claim 1, wherein placing the cement into the wellbore is achieved using a pump.

* * * * *